(12) United States Patent
Santilli

(10) Patent No.: US 6,364,883 B1
(45) Date of Patent: Apr. 2, 2002

(54) SPINOUS PROCESS CLAMP FOR SPINAL FUSION AND METHOD OF OPERATION

(76) Inventor: Albert N. Santilli, 28326 Gates Mills Blvd., Pepper Pike, OH (US) 44124

( * ) Notice: Subject to any disclaimer, the term of this patent is extended or adjusted under 35 U.S.C. 154(b) by 0 days.

(21) Appl. No.: 09/792,696

(22) Filed: Feb. 23, 2001

(51) Int. Cl.[7] ............................................... A61B 17/58
(52) U.S. Cl. .......................................... 606/69; 606/61
(58) Field of Search .............................. 606/69, 70, 72, 606/75, 64, 86, 61, 104, 151; 623/17.11, 17.15, 16.11

(56) References Cited

U.S. PATENT DOCUMENTS

| | | | |
|---|---|---|---|
| 4,773,402 A | * | 9/1988 | Asher et al. .................. 606/69 |
| 5,127,912 A | * | 7/1992 | Ray et al. ..................... 606/61 |
| 5,300,073 A | * | 4/1994 | Ray et al. ..................... 606/61 |
| 5,382,248 A | | 1/1995 | Jacobson et al. |
| 5,611,800 A | | 3/1997 | Davis et al. |
| 6,197,028 B1 | * | 3/2001 | Ray et al. ..................... 606/69 |

* cited by examiner

*Primary Examiner*—Pedro Philogene
(74) *Attorney, Agent, or Firm*—Rankin, Hill, Porter & Clark LLP

(57) ABSTRACT

A spinous process clamp employs a pair of elongate plates that are positioned on either side of the spinous processes of vertebrae that are to be fused. The plates are joined by fasteners, preferably bolts and nuts. When the bolts and nuts are tightened, the spinous processes are clamped between the plates, thereby preventing motion between the clamped vertebral bodies. In an embodiment especially adapted for immobilizing a patient's lower lumbar region, the clamp is provided with projections that engage the patient's sacrum and brackets that are connected to the sacrum. The invention eliminates the use of pedicle screws, wires, or hooks, thereby greatly simplifying the installation process.

19 Claims, 5 Drawing Sheets

SPINOUS PROCESS CLAMP FOR SPINAL FUSION AND METHOD OF OPERATION

BACKGROUND OF THE INVENTION

1. Field of the Invention

The invention relates to spinal fusion surgery and, more particularly, to a clamp useful in such surgery.

2. Description of the Prior Art

Spinal fusion is performed to prevent motion between mobile segments of the spine. A variety of reasons exist for performing spinal fusion. The spine may be unstable due to a traumatic injury, surgery, or invasion and destruction of the vertebrae by tumor. Continued motion of particular segments of the spine may cause overgrowth of joint and ligamentous tissue which, in turn, may compress the spinal cord or its nerves. The curvature of the spine may become abnormal and cause deformity or neurological problems. In these instances, it may be desirable to prevent spinal motion at the affected levels.

The spine is composed of individual bones, or vertebrae, stacked on top of each other in a column. Each vertebra includes a cylindrical vertebral body, which participates in weight bearing, and an arch of bone (comprising the lamina and spinous process) which protects the spinal cord and its coverings. The bony arch is connected to the vertebral body by two small columns of bone, referred to as the pedicles. The circular canal between the body, the arch, and the pedicles houses the spinal cord and is called the spinal canal. Between adjacent vertebral bodies lie the intervertebral discs. These are cartilaginous structures that function as shock absorbers for the spine. Facet joints connect the bony arches of the spine and permit spinal motion between adjacent vertebrae.

Spinal instrumentation is employed as an adjunct to successful spinal fusion. The instrumentation immobilizes the spine while the body forms new, solid bone. Spinal fusion usually is performed by surgically exposing the area of the spine to be fused and thereafter preparing the exposed bone by removing soft tissue and ligaments so new bone can form over the area. After the surgical site has been prepared, an autogenic bone graft (from another part of the body, usually the hip) or an allogenic bone graft (from a cadaver) can be implanted in the prepared area so that new bone can form around and within the implant. Recently, non-biologic implants have been developed in an attempt to avoid the problems associated with acquiring a bone graft implant. Regardless of the type of implant that is used, the chances of achieving a successful fusion are enhanced if motion in the area is minimized or prevented while new bone forms. Since it usually takes from three to 12 months for new bone to form, motion in the affected area must be minimized or prevented for approximately three to 12 months.

Motion during the bone formation period may be prevented by wearing a hard external plastic brace or by installing internal metal instrumentation. Instrumentation usually entails placing screws, hooks, or wires in the affected vertebrae, pedicles, laminae, or spinal joints and then connecting the screws, hooks, or wires to metal rods or a metal plate. The rods or plate act as a solid bridge between the vertebrae, and the screws, hooks, or wires secure the bridge to the vertebrae. This technique reduces or eliminates motion between the vertebrae while bony fusion occurs. An example of a spinal fusion system of the type described is shown by U.S. Pat. No. 5,611,800.

Depending on the area of the spine being fused, the addition of instrumentation may substantially increase the chance of successful fusion as opposed to only wearing an external brace. Spinal instrumentation also may afford immediate spinal rigidity and allow the patient to return to normal physical activity sooner than otherwise possible. The benefits of instrumentation are offset by the potential for problems to occur due to the installation or failure of the instrumentation itself. Surgical procedures involving the placement of instrumentation often require significant time and skill to perform. Risk of injury to nerves or blood vessels in the fusion area may be higher than if instrumentation were not used. The instrumentation may break or cause pain and subsequently may need to be removed. Although the use of instrumentation usually outweighs the risks of not using it, it is desirable to employ the most easy-to-install, reliable form of instrumentation in order to increase the chances that the procedure will be effective.

Desirably, a technique for spinal fusion would be known that would enable two or more vertebral bodies to be joined quickly and easily. Preferably, such a technique would not require the use of screws, wires, or hooks.

SUMMARY OF THE INVENTION

In response to the foregoing concerns, the present invention provides a new and improved technique for spinal fusion. The invention employs a spinous process clamp in which a pair of elongate plates are positioned on either side of the spinous processes of vertebrae that are to be fused. The plates are joined by fasteners, preferably bolts and nuts. When the bolts and nuts are tightened, the spinous processes are clamped between the plates, thereby preventing motion between the clamped vertebral bodies.

In an alternative embodiment of the invention intended particularly to immobilize the lumbar region of the spine, projections are provided to extend from the lower end of the plates. The projections engage the upper portion of the patient's sacrum and stabilize it relative to the vertebral bodies. If desired, brackets can be provided to connect the lower end of the plates to the upper portion of the sacrum. In this instance, bone screws are used to connect the brackets to the sacrum.

By providing the plates in a variety of sizes and configurations, the surgeon can quickly and easily immobilize a desired portion of a patient's spine. Significantly, no drilling is required to install the clamp according to the invention (except for the sacral bracket, if one is used), thereby eliminating the use of pedicle screws, wires, or hooks.

DESCRIPTION OF THE PREFERRED EMBODIMENT

Figure 1:
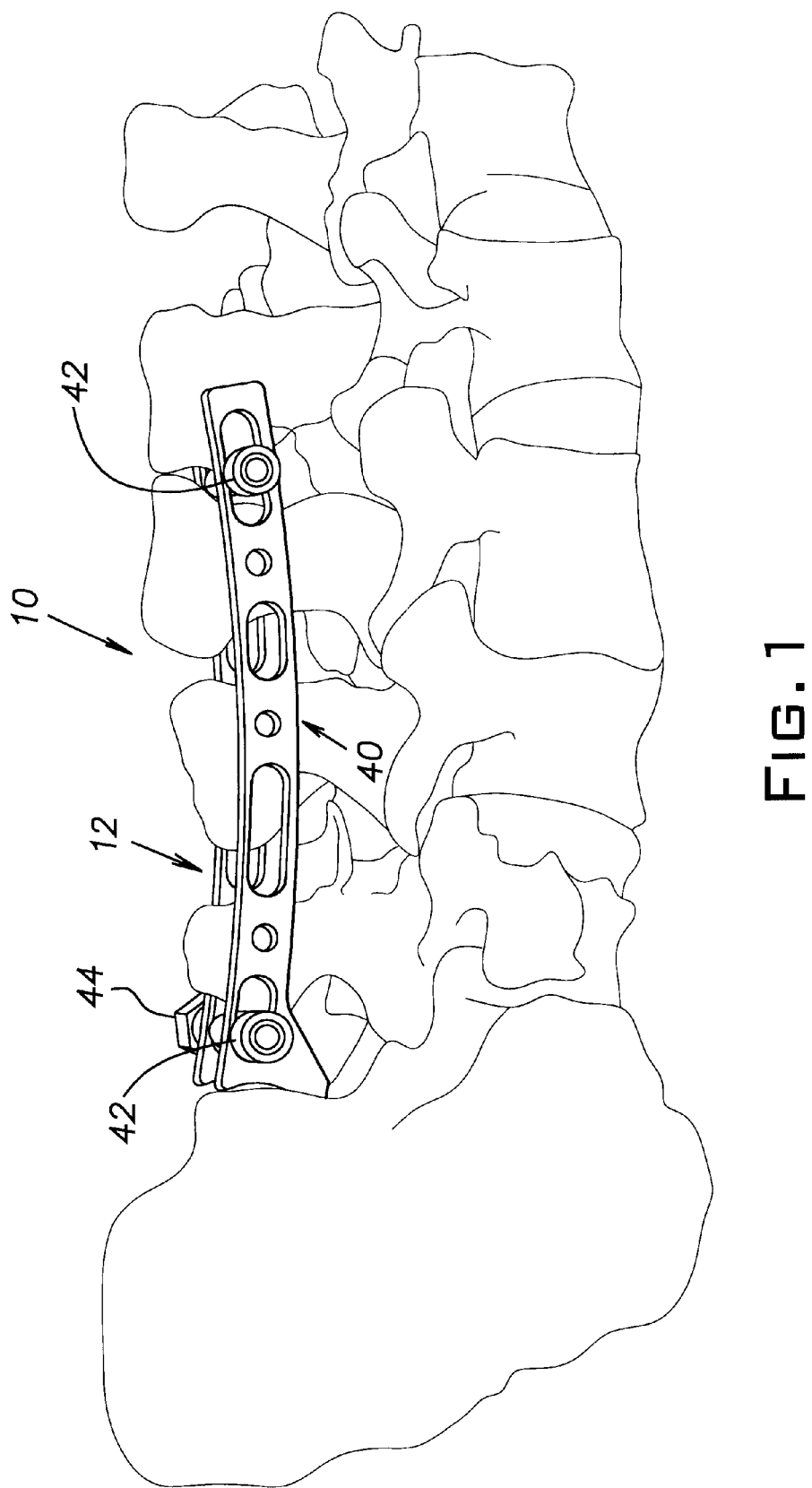
FIG. 1 is a side elevation view of a clamp according to the invention connected to the lumbar region of a model of a patient's spine.
Figure 2:
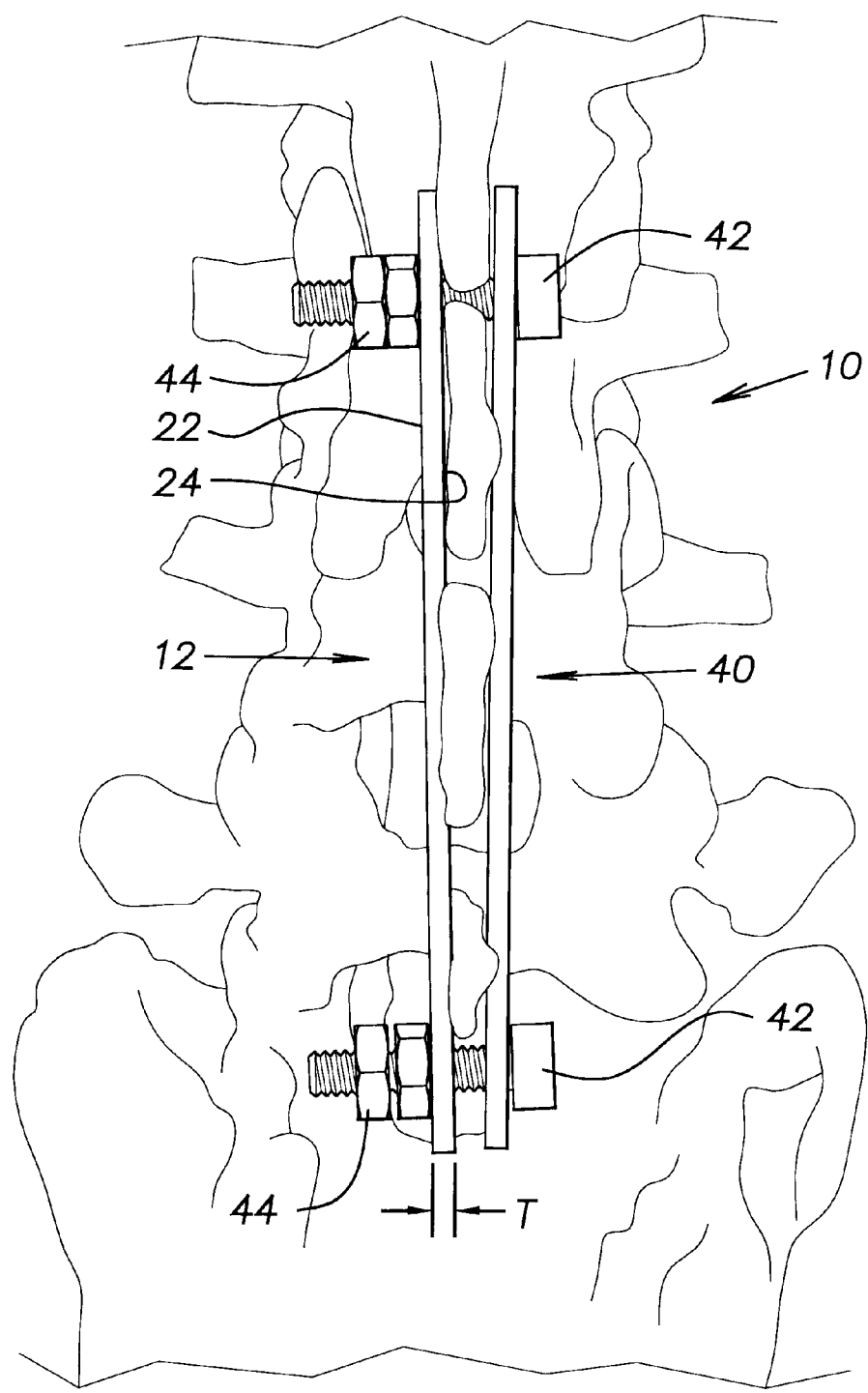
FIG. 2 is a posterior view of the clamp of FIG. 1.
Figure 5:
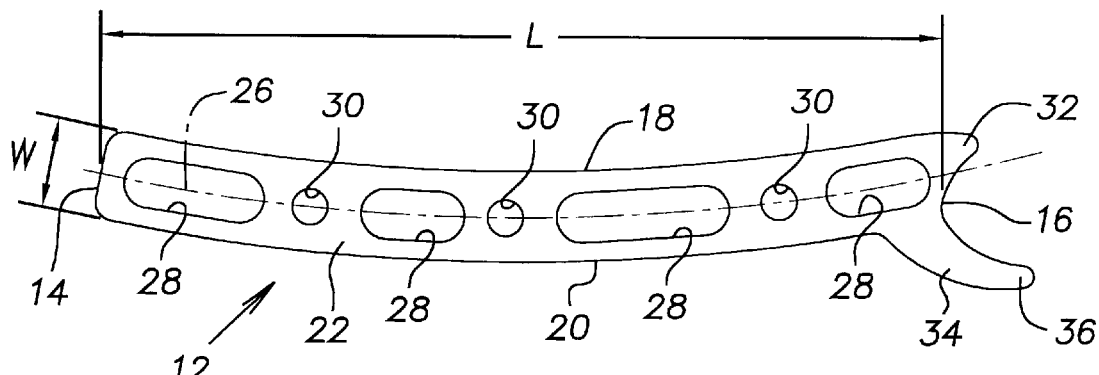
FIG. 5 is a side elevation view of a plate included as part of the clamp of FIG. 1.

Referring to FIGS. 1 and 2, a spinous process clamp according to the invention is indicated generally by the reference numeral 10. The clamp 10 is illustrated as immobilizing the lumbar spine. Referring also to FIG. 5, the clamp 10 includes a first, generally flat plate 12. The plate 12 has an overall length (L), a thickness (T), and a width (W), the dimensions of which can be selected to suit the needs of a particular patient. The plate 12 has a first end 14 and a second end 16 spaced apart the length (L), a posterior edge 18 and an anterior edge 20 spaced apart the width (W), and a first side 22 and a second side 24 spaced apart the thickness (T). The plate 12, when viewed from the side, is curved to define a concave surface on the posterior edge 18 and a convex surface on the anterior edge 20. The plate 12 is straight when viewing either edge 18 or 20 face-on, that is, the first and second sides 22, 24 lie in parallel planes. The plate 12 has a curved longitudinal axis 26 and a plurality of elongate openings 28 spaced along the longitudinal axis 26. A plurality of small, round openings are disposed intermediate the elongate openings 28.

The first end 14 is flat. The second end 16 includes a first, small, rounded projection 32 that extends from the intersection of the posterior edge 18 and the second end 24 as a continuation of the posterior edge 18. A second, large, tapered projection 34 extends from the anterior edge 20 at the intersection between the anterior edge 20 and the second end 16. The second projection 34 is rounded at its end as indicated by the reference numeral 36.

Typical dimensions for the plate 12 when used to immobilize the lumbar spine are a length of 4.5 inches, a width of 0.4375 inch, and a thickness of 0.1875 inch. The radius of curvature of the longitudinal axis 26 is a constant 12.0 inches. The projection 32 has a radius of approximately 0.10 inch. The base of the projection 34 has a width of approximately 0.50 inch. The projection 34 extends approximately 0.25 inch from the anterior edge 20, and the rounded end 36 has a radius of approximately 0.10 inch. The openings 28 are of two lengths: 0.75 inch and 0.50 inch. The width of the openings 28 is approximately 0.25 inch. The openings 30 have a diameter of approximately 0.125 inch. The plate 12 is made of a strong, biologically inert material such as 302 stainless steel, titanium or a titanium alloy.

The clamp 10 includes a second plate 40 that is substantially identical to the first plate 12. A plurality of fasteners in the form of bolts 42 extend through selected openings 28 in the first and second plates 12, 40, the bolts 42 being of a length that will permit a patient's spinous processes to be clamped between the first and second plates 12, 40. A plurality of hexagonal nuts 44 are provided for the bolts 42. The bolts 42 typically are 1.375 inches long and 0.1875 inch in diameter. The bolts 42 have recessed socket heads that will receive a suitably sized Allen wrench. The bolts 42 and the nuts 44 preferably are made of the same material as the plates 12, 40.

Figure 3:
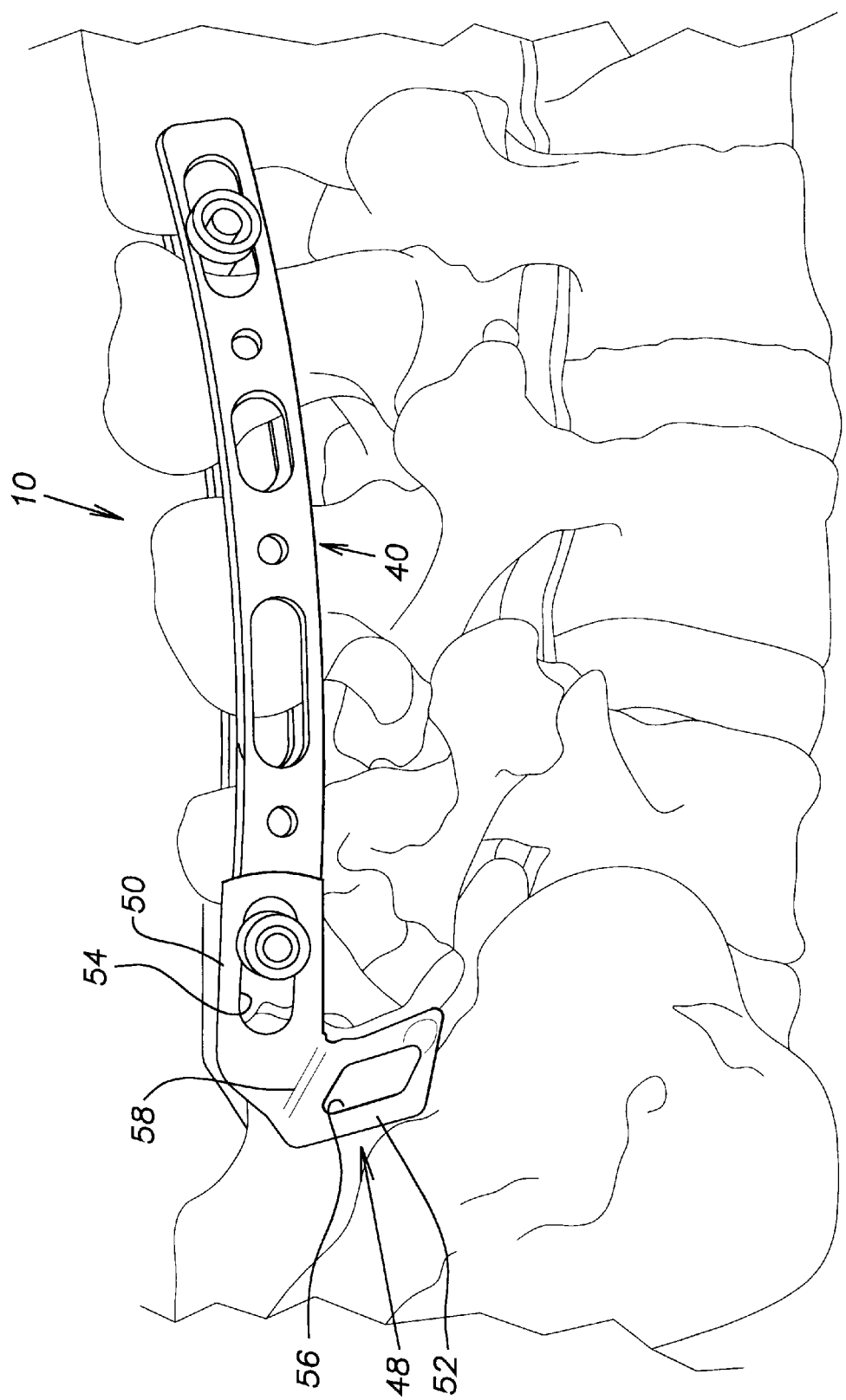
FIG. 3 is a view of the clamp of FIG. 1, including a bracket that connects the clamp to the sacrum.
Figure 4:
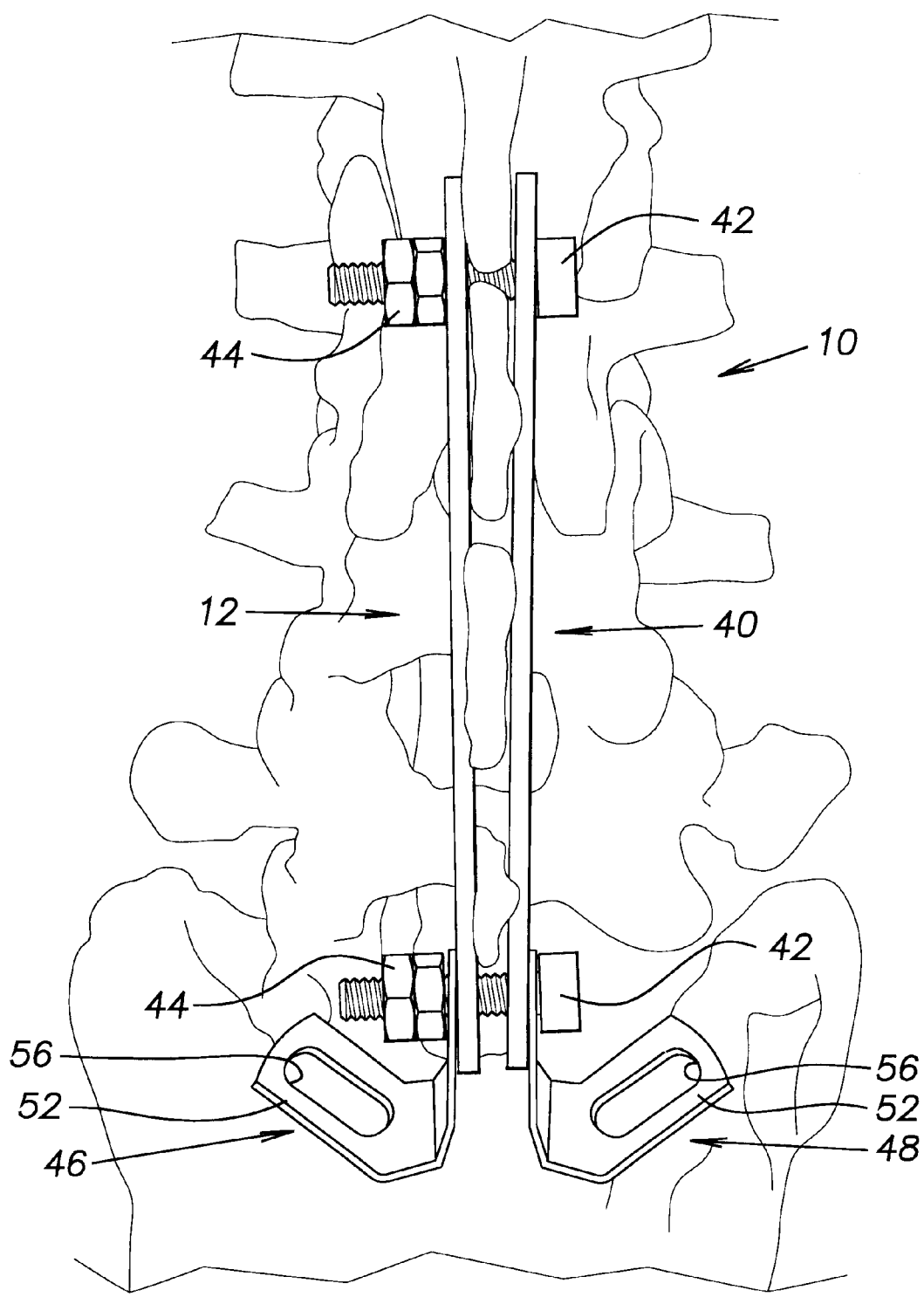
FIG. 4 is a posterior view of the clamp of FIG. 3.

Referring to FIGS. 3 and 4, a pair of brackets 46, 48 connect the second end 16 to the sacrum. The brackets 46, 48 are mirror images of each other. Each bracket includes a first leg 50 and a second leg 52. Each leg 50 has an elongate opening 54 through which one of the bolts 42 can pass. Each leg 52 has an elongate opening 56 through which a bone screw (not shown) can be passed as the screw is inserted into the sacrum. The brackets 46, 48 preferably are formed flat in a stamping operation and then bent at approximately right angles about a bend line indicated by the reference numeral 58. The legs 50, 52 are about one inch long. The brackets 46, 48 preferably are made of the same material as the plates 12, 40. Referring particularly to FIG. 4, the legs 52 are reversely bent relative to the legs 50 to extend away from the plates 12, 40 at an angle of about 65 degrees. It will be appreciated that this angle can be varied considerably in order to suit the needs of a particular patient.

Figure 6:
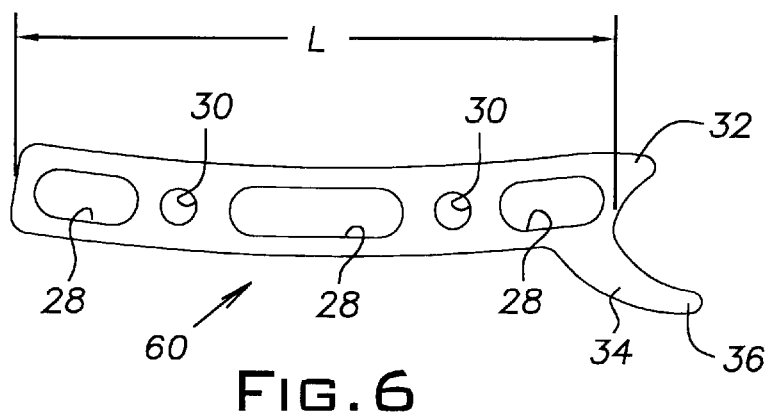
FIGS. 6 and 7 are side elevation views of two additional embodiments of a plate according to the invention.
Figure 7:
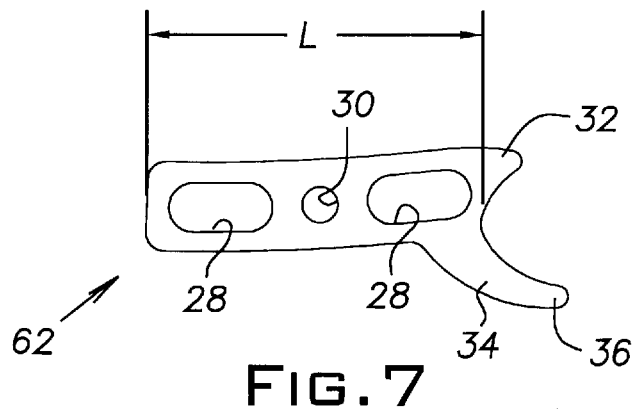

Referring to FIG. 6, an alternative embodiment of a plate used as part of a clamp according to the invention is indicated by the reference numeral 60. The plate 60 is substantially similar to the plates 12, 40 except that its length (L) is 3.125 inches. With the exception that the plate 60 has fewer openings 28, 30, the plate 60 is identical to the plates 12, 40. In FIG. 7, yet another embodiment of a plate according to the invention is indicated by the reference numeral 62. the plate 62 has a length (L) of 1.75 inches. With the exception that the plate 62 has fewer openings 28, 30, the plate 62 is identical to the plates 12, 40. Because the plates 60, 62 are shorter than the plates 12, 40, their use would be indicated in those cases where fewer vertebral bodies need to be immobilized.

The clamp 10 has been illustrated as it would be used to immobilize a portion of the lumbar spine, but it will be appreciated that the clamp 10 can be used to immobilize other portions of the spine upon suitable reconfiguration of the plates 12, 40 to conform to the region of the spine to be immobilized. In any such reconfiguration, projections 32, 34 and the brackets 46, 48 would be eliminated, and the radius of curvature of the plates 12, 40 would be adjusted to conform to the portion of the spine to be immobilized. If desired, the thickness (T) can be varied along the length of the plates 12, 40 in order to better conform to the shape of a patient's spinous processes. Also, the size and shape of the legs 50, 52 of the brackets 46, 48 can be varied to suit the needs of different patients.

In view of the changes that can be made to the invention, it will be understood that the present disclosure of the preferred embodiment has been made only by way of example, and that various changes may be resorted to without departing from the true spirit and scope of the invention as hereinafter claimed. It is intended that the patent shall cover, by suitable expression in the appended claims, whatever degree of patentable novelty exists in the invention disclosed.

What is claimed is:

1. A spinous process clamp for spinal fusion, comprising:
   a first plate having an overall length (L) and a width (W), the first plate having a first end and a second end spaced apart the length (L), a posterior edge and an anterior edge spaced apart the width (W), the first plate when viewed from the side being curved about a longitudinal axis that approximately conforms to the radius of curvature of the portion of the patient's spine to be immobilized, and a plurality of openings spaced along the longitudinal axis;
   a second plate that is substantially identical to the first plate; and
   a plurality of fasteners adapted to extend through the openings in the first and second plates, the fasteners being of a length that will permit a patient's spinous processes to be clamped between the first and second plates.

2. The clamp of claim 1, wherein the radius of curvature of the longitudinal axis is constant.

3. The clamp of claim 2, wherein the radius of curvature of the longitudinal axis is approximately 12.0 inches.

4. The clamp of claim 1, wherein the length (L) is within the range of approximately 3.125 to 4.75 inches and the width (W) is approximately 0.4375 inch.

5. The clamp of claim 1, wherein the first and second plates are flat, and each has a thickness (T) that is constant along the length of the plate.

6. The clamp of claim 5, wherein the thickness (T) is approximately 0.1875 inch.

7. The clamp of claim 1, further comprising a pair of projections extending from the second end, the projections being of a size and shape to conform to the upper portion of the patient's sacrum.

8. The clamp of claim 7, wherein the projections include a rounded end.

9. The clamp of claim 1, further comprising a connection between the plates and the patient's sacrum.

10. The clamp of claim 9, wherein the connection between the plates and the patient's sacrum includes:

a pair of bone screws;

a bracket for each of the plates, each bracket having first and second legs, the first leg adapted to be connected to the second end of a selected plate and the second leg adapted to be connected to the patient's sacrum;

each of the first and second legs having an opening; the first leg being connected to the second end by a fastener that extends through the opening in the first leg; and the second leg being connected to the sacrum by a bone screw that extends through the opening in the second leg.

11. The clamp of claim 1, wherein the fasteners are bolts and nuts.

12. A spinous process clamp for spinal fusion, comprising:

a first, generally flat plate having an overall length (L), a thickness (T), and a width (W), the first plate having a first end and a second end spaced apart the length (L), opposed sides spaced apart a distance equal to the thickness (T), and a posterior edge and an anterior edge spaced apart the width (W), the first plate when viewed from the side being curved, and when viewed from the front being straight, the plate having a curved longitudinal axis that approximately conforms to the radius of curvature of the portion of the patient's spine to be immobilized and a plurality of openings spaced along the longitudinal axis;

a second plate that is substantially identical to the first plate;

a plurality of bolts adapted to extend through the openings in the first and second plates, the bolts being of a length that will permit a patient's spinous processes to be clamped between the first and second plates; and a plurality of nuts adapted to be threaded onto the bolts to clamp the plates in place.

13. The clamp of claim 12, wherein the radius of curvature is constant and is approximately 12.0 inches.

14. The clamp of claim 12, wherein the length (L) is within the range of approximately 3.125 to 4.75 inches, the thickness (T) is approximately 0.1875 inch, and the width (W) is approximately 0.4375 inch.

15. The clamp of claim 12, further comprising a pair of projections extending from the second end, the projections being of a size and shape to conform to the upper portion of the patient's sacrum, each of the projections including a rounded end.

16. The clamp of claim 12, further comprising a connection between the plates and the patient's sacrum that includes:

a pair of bone screws;

a bracket for each of the plates, each bracket having first and second legs, the first leg adapted to be connected to the second end of a selected plate and the second leg adapted to be connected to the patient's sacrum;

each of the first and second legs having an opening;

the first leg being connected to the second end by a fastener that extends through the opening in the first leg; and the second leg being connected to the sacrum by a bone screw that extends through the opening in the second leg.

17. A method of spinal fusion, comprising the steps of:

providing a first plate having an overall length (L) and a width (W), the first plate having a first end and a second end spaced apart the length (L), a posterior edge and an anterior edge spaced apart the width (W), the first plate when viewed from the side being curved, the plate having a curved longitudinal axis and a plurality of openings spaced along the longitudinal axis;

providing a second plate that is substantially identical to the first plate;

providing a plurality of fasteners adapted to extend through the openings in the first and second plates, the fasteners being of a length that will permit a patient's spinous processes to be clamped between the first and second plates;

disposing the first and second plates on either side of a patient's spinous processes with the openings in the plates in alignment with each other and with spaces between the patient's spinous processes;

inserting the fasteners through selected openings in the plates and the spaces between the patient's spinous processes; and tightening the fasteners until the spinous processes disposed between the plates are clamped securely.

18. The method of claim 17, further comprising the steps of:

providing the first and second plates with a pair of projections extending from the second end, the projections being of a size and shape to conform to the upper portion of the patient's sacrum; and placing the projections against the patient's sacrum prior to the steps of inserting the fasteners and tightening the fasteners.

19. The method of claim 17, further comprising the steps of:

providing a bracket for each of the plates, each bracket having first and second legs, each of the first and second legs having an opening;

disposing the first leg of each bracket adjacent the second end of a selected plate and the second leg of each bracket adjacent the patient's sacrum;

providing a pair of bone screws;

extending a fastener through the opening in the first leg of each bracket and the spaced-apart plates prior to the step of tightening the fasteners;

drilling an opening in the patient's sacrum in alignment with the opening in the second leg of each bracket; and inserting a bone screw through the opening in the second leg of each bracket into the opening in the sacrum, whereby the brackets will be secured to the sacrum.

* * * * *